United States Patent [19]
Isogai et al.

[11] Patent Number: 5,637,949
[45] Date of Patent: Jun. 10, 1997

[54] PIEZOELECTRIC ACTUATOR SENSITIVE TO REDUCING GAS

[75] Inventors: Yuji Isogai, Saitama-ken; Hiroaki Yanagida, Chofu; Masaru Miyayama, Kawasaki, all of Japan

[73] Assignee: Honda Giken Kogyo Kabushiki Kaisha, Tokyo, Japan

[21] Appl. No.: 545,003

[22] Filed: Oct. 30, 1995

[30] Foreign Application Priority Data

Oct. 31, 1994 [JP] Japan .................................. 6-290653
May 29, 1995 [JP] Japan .................................. 7-153878

[51] Int. Cl.$^6$ .................................................. H01L 41/08
[52] U.S. Cl. .................................................. 310/330; 310/331
[58] Field of Search .................................. 310/330, 331

[56] References Cited

U.S. PATENT DOCUMENTS

| | | | |
|---|---|---|---|
| 3,646,413 | 2/1972 | Oomen | 317/246 |
| 4,533,849 | 8/1985 | Schnell | 310/330 |
| 4,564,851 | 1/1986 | Nilsson et al. | 346/140 R |
| 4,707,311 | 11/1987 | Okazaki | 24/43 |
| 4,885,929 | 12/1989 | Kasahara et al. | 73/23 |
| 5,068,567 | 11/1991 | Jones | 310/332 |
| 5,140,393 | 8/1992 | Hijikihigawa et al. | 357/29 |
| 5,224,972 | 7/1993 | Frye et al. | 55/18 |
| 5,382,864 | 1/1995 | Morikawa et al. | 310/332 |
| 5,461,274 | 10/1995 | Yuji et al. | 310/330 |

Primary Examiner—Thomas M. Dougherty
Attorney, Agent, or Firm—Lyon & Lyon LLP

[57] ABSTRACT

A piezoelectric actuator subjected to bending displacement by sensing a reducing gas is composed of two regions bonded to each other, one of the regions being made of a material whose electric resistance varies by sensing a reducing gas, and the other of the regions being made of a piezoelectric material which is not sensitive to a reducing gas, an electrode being formed on an outer surface of each region to apply an electric field to the piezoelectric material.

11 Claims, 5 Drawing Sheets

PIEZOELECTRIC ACTUATOR SENSITIVE TO REDUCING GAS

BACKGROUND OF THE INVENTION

The present invention relates to a piezoelectric actuator subjected to bending displacement by sensing a reducing gas such as a carbon monoxide gas, a hydrogen gas, etc., and more particularly to a piezoelectric actuator suitable for operating valves, etc. by sensing a reducing gas such as a carbon monoxide gas, a hydrogen gas, etc. in an apparatus or equipment which may generate such a reducing gas.

Exhaust gases discharged from internal engines, combustion apparatuses, etc. may contain reducing gases such as a carbon monoxide gas, a hydrogen gas, etc. Since the reducing gases are harmful to human beings and cause air pollution, the generation of such reducing gases should be suppressed. For this purpose, a reducing gas sensor is used, but a widely used reducing gas sensor is constituted separately from an actuator, so that the actuator is operated in response to an output signal of the sensor to drive a control valve or to change combustion conditions. However, with such a separate structure, wiring of the reducing gas sensor, an actuator, a controller (for instance, computer), etc. is extremely complicated, making the overall structure of the apparatus complicated, and making it difficult to check and repair the apparatus.

OBJECT AND SUMMARY OF THE INVENTION

Accordingly, an object of the present invention is to provide a reducing gas-sensitive piezoelectric actuator integrally comprising a reducing gas-sensing function and an actuator function.

As a result of research in view of the above object, the inventors have found that by laminating a region made of a zinc oxide ceramic sensitive to a reducing gas and a region made of a piezoelectric material insensitive to the reducing gas, it is possible to obtain a piezoelectric actuator subjected to bending displacement by sensing a reducing gas. The present invention has been completed based on this finding.

Thus, the piezoelectric actuator subjected to bending displacement by sensing a reducing gas according to the present invention is composed of two regions bonded to each other, one of the regions being made of a material whose electric resistance varies by sensing a reducing gas, and the other of the regions being made of a piezoelectric material which is not sensitive to a reducing gas, an electrode being formed on an outer surface of each region to apply an electric field to the piezoelectric material.

DETAILED DESCRIPTION OF THE PREFERRED EMBODIMENTS

Figure 1:
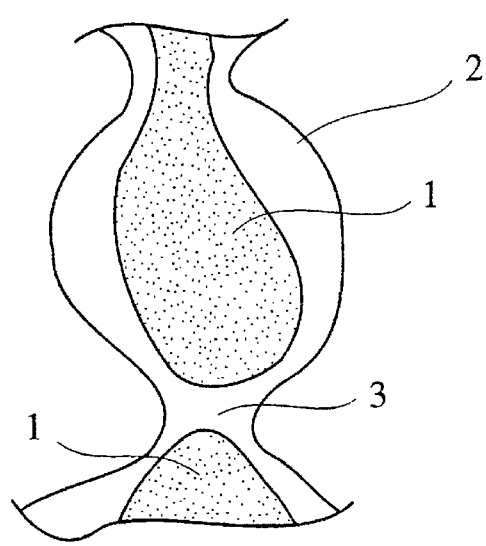
FIG. 1 is a schematic view showing the formation of a potential barrier due to the absorption of oxygen to a surface of a ZnO ceramic.

A ZnO ceramic useful for a reducing gas sensor has a characteristic that a potential barrier in which carriers ($e^{-1}$) are decreased is formed on its surface when $O_2$ is absorbed onto the surface. Thus, as shown in FIG. 1, if the ZnO ceramic is porous, substantially all surface layers of ZnO particles 1 are turned deeply into high-resistance layers 2. Since bonding phases between ZnO particles 1 are narrow in the porous ZnO ceramics, such bonding phases constitute neck portions 3 comprising of high-resistance layers 2 only. As a result, the ZnO ceramics are extremely high in electric resistance in an oxidizing atmosphere containing $O_2$. However, if there is a reducing gas, the high-resistance layers 2 are decreased because oxygen absorbed onto the ZnO particles decreases, resulting in an increase in carriers ($e^{-1}$). Thus, the ZnO ceramics have a reduced electric resistance.

Figure 2A:
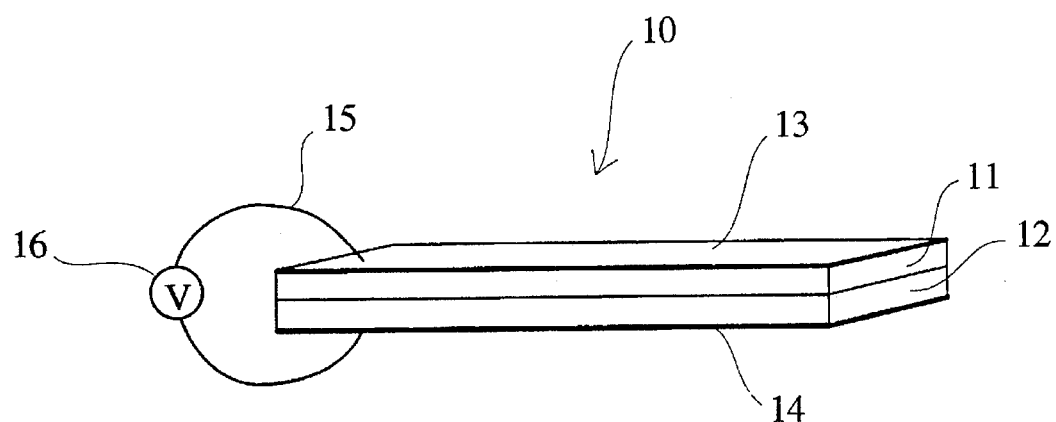
FIG. 2(a) is a schematic view showing the piezoelectric actuator according to the present invention.
Figure 2B:
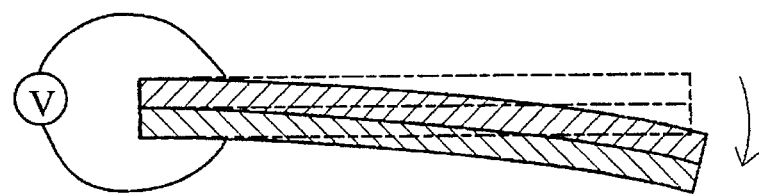
FIG. 2(b) is a cross-sectional view of the piezoelectric actuator of FIG. 2(a) which was subjected to bending displacement by applying an electric field.

FIG. 2(a) shows a bimorph-type piezoelectric actuator 10 comprising a reducing gas-sensitive region 11 made of a porous ZnO ceramic, a region 12 made of a piezoelectric material insensitive to a reducing gas and laminated to the reducing gas-sensitive region 11, and electrodes 13, 14 formed on both surfaces thereof. If there is a reducing gas, the electric resistance of the ZnO ceramic region 11 decreases, leading to an increase in voltage in the piezoelectric material region 12. As a result, the piezoelectric material region 12 shows an increased shrinkage in the longitudinal direction (perpendicular to the direction of an electric field applied). Since the ZnO ceramic region 11 does not shrink, the bimorph-type piezoelectric actuator 10 is subjected to bending displacement as shown in FIG. 2(b).

The bimorph-type piezoelectric actuator of the present invention utilizes this principle, exhibiting a function to convert the sensing of a reducing gas to a mechanical displacement.

The present invention will be explained in detail below referring to the drawings attached hereto.

[1] Layer structure of piezoelectric actuator (1) Reducing gas-sensitive region (a) Composition The material of this region is mainly zinc oxide ceramic (ZnO). However, since ZnO has an extremely low electric resistance as compared with a piezoelectric material, the electric resistance of zinc oxide ceramic should be increased to the same level as or more than that of the piezoelectric material in the case of lamination to a bimorph type. For this purpose, nickel oxide (NiO) and lithium oxide (LiO) are preferably added.

The content of NiO is 2–20 mol %, preferably 5–15 mol % If the content of NiO is less than 2 mol %, the zinc oxide ceramic has a too low electric resistance, showing a low reducing gas sensitivity. On the other hand, if the content of NiO exceeds 20 mol %, the reducing gas sensitivity of the zinc oxide ceramic decreases.

The content of LiO is 0.2–1 mol %, preferably 0.2–0.5 mol %. If the content of LiO is less than 0.2 mol %, the zinc oxide ceramic has a too low electric resistance, showing a low reducing gas sensitivity. On the other hand, if the content of LiO exceeds 1 mol %, sintering is accelerated, resulting in a low reducing gas sensitivity. Since LiO has a function of selectively increasing a sensitivity to a carbon monoxide (CO), it is effective particularly when the sensitivity to a CO gas is to be increased.

(b) Density

In order that the zinc oxide ceramic is highly sensitive to a reducing gas, it is preferably porous. Specifically, the zinc oxide ceramic has a relative density of preferably 40–80%, more preferably 50–70%. If the relative density of the zinc oxide ceramic is lower than 40%, the zinc oxide ceramic shows insufficient mechanical strength. On the other hand, if it exceeds 80%, the zinc oxide ceramic shows a decreased sensitivity to a reducing gas.

(2) Piezoelectric region (a) Composition

The piezoelectric material used in the present invention is preferably lead titanate zirconate [$Pb(Zr, Ti)O_3$, simply called "PZT"]. To improve its piezoelectric properties, 5 mol % or less, particularly 0.5–3 mol % of $Nb_2O_5$ may preferably be added to PZT. However, more than 2 mol % of $Nb_2O_5$ undesirably makes the piezoelectric material brittle.

(b) Density

Lead titanate zirconate should have a high density, and its relative density is preferably 80% or more. If the relative density of lead titanate zirconate is less than 80%, the piezoelectric region shows poor piezoelectric properties.

(3) Electrode (a) Electrode on the side of reducing gas-sensitive region

In order that the zinc oxide ceramic layer is sensitive to a reducing gas, the electrode should be porous. Accordingly, the electrode is preferably formed by sputtering Ag, Au, Pt, In-Ga alloys, etc. As long as a porous electrode is obtained, the thickness of the electrode is not particularly restricted.

(b) Electrode on the side of piezoelectric region

The electrode on the side of the piezoelectric region need not be porous, and may be formed by any known methods such as a paste coating method, a plating method, etc. Metals for this electrode may be Ag, Au, Pt, In-Ga alloys, etc.

(4) Thickness of each layer

The thickness of the reducing gas-sensitive region is preferably 100–1000 μm, particularly 200–700 μm. Also, the thickness of the piezoelectric region is preferably 100–1000 μm, particularly 200–700 μm. The thickness of each electrode is not restrictive; an electrode sputtered onto the surface of the reducing gas-sensitive region may be 50–1000 Å, and an electrode on the surface of the piezoelectric region may be 5–50 μm.

(5) Intermediate layer

Since the zinc oxide ceramic forming the reducing gas-sensitive region and PZT forming the piezoelectric region have different thermal expansion coefficients, a stress of bending displacement is concentrated in an interface between these two layers, thereby making it likely to cause peeling and breakage. To prevent them, it is preferable to form a mixture layer of both materials as an intermediate layer in the interface. The composition of the mixture layer is preferably 8/2–2/8 of ZnO/PZT by weight.

The intermediate layer is formed such that it has an intermediate density between those of the zinc oxide ceramic and PZT. To this end, sintering temperature and pressure may be controlled. Also, the thickness of the intermediate layer may be about 50–200 μm, though it is not restrictive as long as drastic change of density is avoided.

(6) Operation of piezoelectric actuator

The piezoelectric actuator of the present invention is preferably operated at a temperature of 250°–350° C. to achieve a high sensitivity to a reducing gas and to keep good piezoelectric properties of PZT. Such a relatively low operating temperature can be achieved by adding NiO and LiO to ZnO (pure ZnO shows a good sensitivity to a reducing gas at such a high temperature as about 400° C.). When the operating temperature exceeds 350° C., the temperature is too close to the Curie temperature of PZT, resulting in a loss of piezoelectric properties of PZT.

An electric field at which the piezoelectric actuator of the present invention is operated is preferably 1–5 kV/cm. If the electric field is lower than 1 kV/cm, the bending displacement of the piezoelectric actuator in the presence of a reducing gas would be small. On the other hand, if it is higher than 5 kV/cm, the piezoelectric actuator is likely to be broken.

[2] Production of piezoelectric actuator (1) Production of green body for reducing gas-sensitive region To form the reducing gas-sensitive region with a zinc oxide ceramic, ZnO powder, $LiNO_3$ powder and NiO powder as starting materials are metered to the above composition and mixed in a ball mill. The ball milling of the starting materials is preferably conducted for 5–50 hours. Next, the mixed powder is calcinated at 500°–650° C. for 3–10 hours. The calcinated powder is formed to a green body having a relative density of 30–50%.

(2) Production of sintered body for piezoelectric region

As starting materials for PZT, PbO powder, $ZrO_2$ powder, $TiO_2$ powder and $Nb_2O_5$ powder are metered to a predetermined composition, mixed in a ball mill and calcinated at 600°–950° C. for 3–10 hours. The resultant calcinated powder is formed to a green body having a relative density of 30–80%. Next, the green body is sintered at 1000°–1200° C. for 2–6 hours.

(3) Lamination and sintering

The zinc oxide ceramic green body is laminated onto the PZT sintered body and sintered under pressure to bond them to each other. To achieve strong bonding, it is preferable to apply a glass frit to their interface. Since glass has a large electric resistance, it is necessary to apply a glass frit as thin as possible to obtain a porous glass layer.

After lamination, sintering is conducted at 7–10 MPa and 650°–800° C. for 1–3 hours to obtain a bimorph-type laminate in which both layers are strongly bonded. Sintering pressure is needed to achieve a sufficient bonding strength, and lower than 7 MPa of sintering pressure would result in too small bonding strength. On the other hand, if the sintering pressure exceeds 10 MPa, the zinc oxide ceramic layer would have a too high density. With respect to the sintering temperature, if it is lower than 650° C. the resultant bonding strength is insufficient, and if it exceeds 800° C. the zinc oxide ceramic layer would have a too high density. Sintering under such conditions is preferably hot pressing.

After machining the laminate to a predetermined dimension, the zinc oxide ceramic layer is formed with an electrode by a sputtering method, a deposition method, etc., and the PZT layer is formed with an electrode by coating an electrode metal paste and baking it. Thus, the desired bimorph-type piezoelectric actuator is obtained.

The present invention will be explained in further detail by the following Examples without intention of restricting the scope of the present invention defined by the claims attached hereto.

EXAMPLE 1

ZnO powder was mixed with NiO powder in an amount of 0 mol %, 2 mol %, 5 mol % and 10 mol %, respectively, ball-milled for 8 hours, and calcinated at 600° C. for 5 hours. The resultant calcinated powder was formed under 0.5 ton/cm$^2$ in a die to obtain green bodies of 15 mm in diameter and 2 mm in thickness. These green bodies were sintered at 700° C. and 8 MPa for 1 hour to obtain porous zinc oxide ceramics (Samples A–D) each having a relative density of 51%. ZnO particles in the samples had an average diameter of 0.4 μm.

Each sample was coated on both surfaces with an Au electrode by sputtering, and the sample was placed in a reactor with the electrodes connected to an outside measuring apparatus. During passing an air at 250° C., 4000 ppm of a CO gas was added to the air flow for 5 minutes to measure the change of electric resistance of the sample. The relations between electric resistivity (Ω·cm) and measurement time are shown for each sample in FIG. 3.

Figure 3:
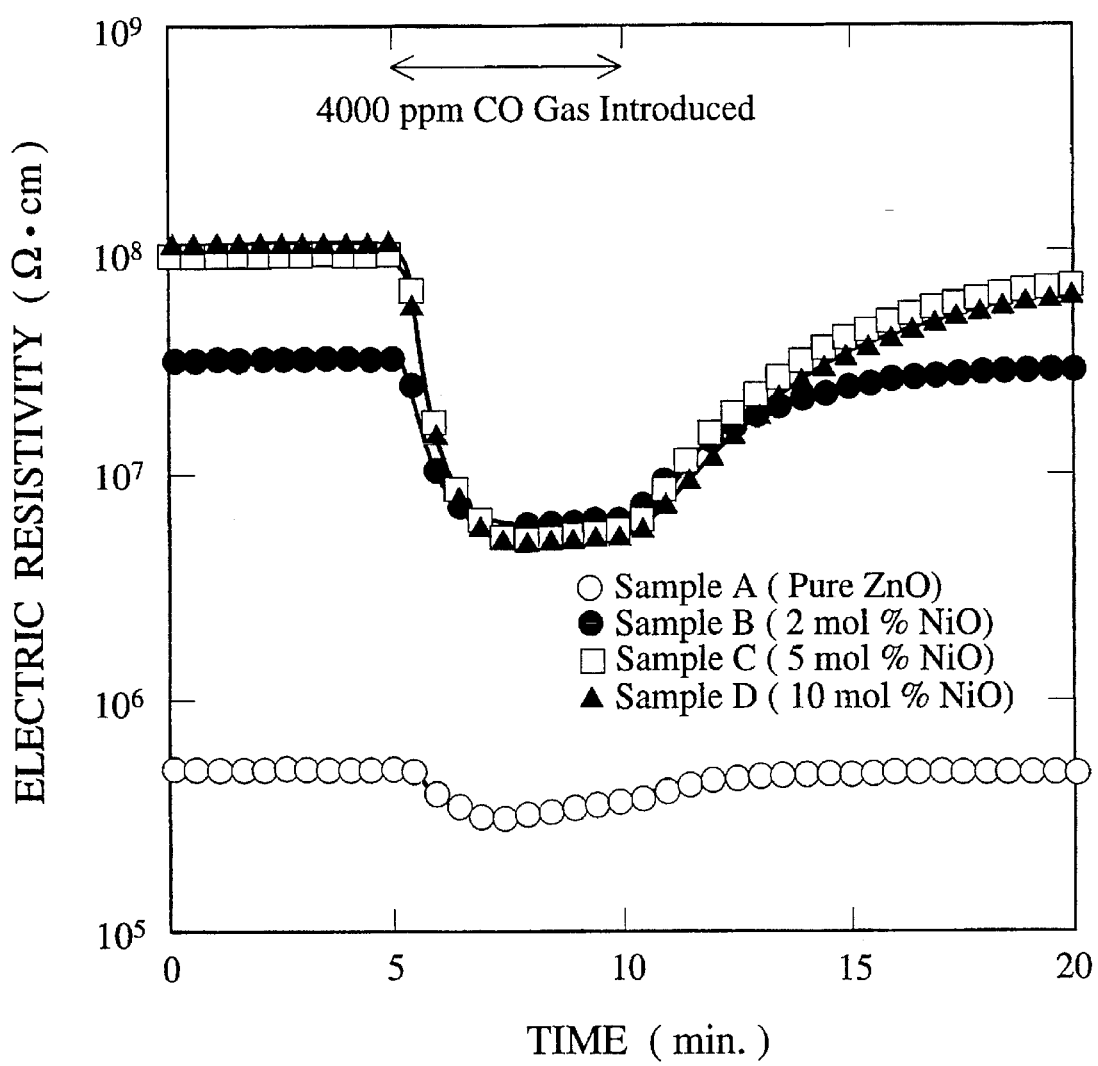
FIG. 3 is a graph showing the change of the electric resistance of zinc oxide ceramic sintered bodies containing various amounts of NiO with time in a case where the sintered bodies were placed in an air containing a CO gas.

As is clear from FIG. 3, in the case of Sample A (pure ZnO), the electric resistivity was less than $10^6$ ·cm, extremely low in a sensitivity to a CO gas. However, as the amount of NiO added to ZnO increased, the electric resistivity and the sensitivity to a CO gas increased.

EXAMPLE 2

ZnO powder was mixed with 10 mol % of NiO powder and 0.2 mol % of LiO powder, and formed into a green body under the same conditions as in Example 1. This green body was hot-pressed at 700° C. and 8 MPa for 1 hour to obtain a porous zinc oxide ceramic (Sample E) having a relative density of 51%. ZnO particles in the sample had an average diameter of 0.4 μm.

Sample E was coated on both surfaces with an Au electrode by sputtering, and placed in a reactor. During passing an air at 250° C., 4000 ppm of a CO gas and 4000 ppm of an H$_2$ gas were added to the air flow for 5 minutes to measure the change of electric resistance of Sample E. The relations between electric resistivity (Ω·cm) and measurement time are shown in FIG. 4.

To obtain a PZT composition of Pb$_{0.995}$Nb$_{0.01}$(Zr$_{0.53}$Ti$_{0.47}$)$_{0.99}$O$_3$, PbO powder, ZrO$_2$ powder, TiO$_2$ powder and Nb$_2$O$_5$ powder were metered and ball-milled in ethanol for 50 hours, and then calcinated at 850° C. for 6 hours. The calcinated powder was ball-milled again for 50 hours, and then pressed at 0.5 tons/cm$^2$ in a disc-shaped die to form a PZT green body of 18 mm in diameter and 2 mm in thickness. The PZT green body was sintered at 1150° C. for 2 hours to obtain a high-density PZT sintered body (Sample F) having a relative density of 98% and containing crystal grains having an average diameter of 5.0 μm.

Sample F was coated on both surfaces with an Ag electrode by a paste coating method, and measured with respect to a sensitivity to 4000 ppm of a CO gas and 4000 ppm of an H$_2$ gas under the same conditions as above. The results are shown in FIG. 4.

Figure 4:
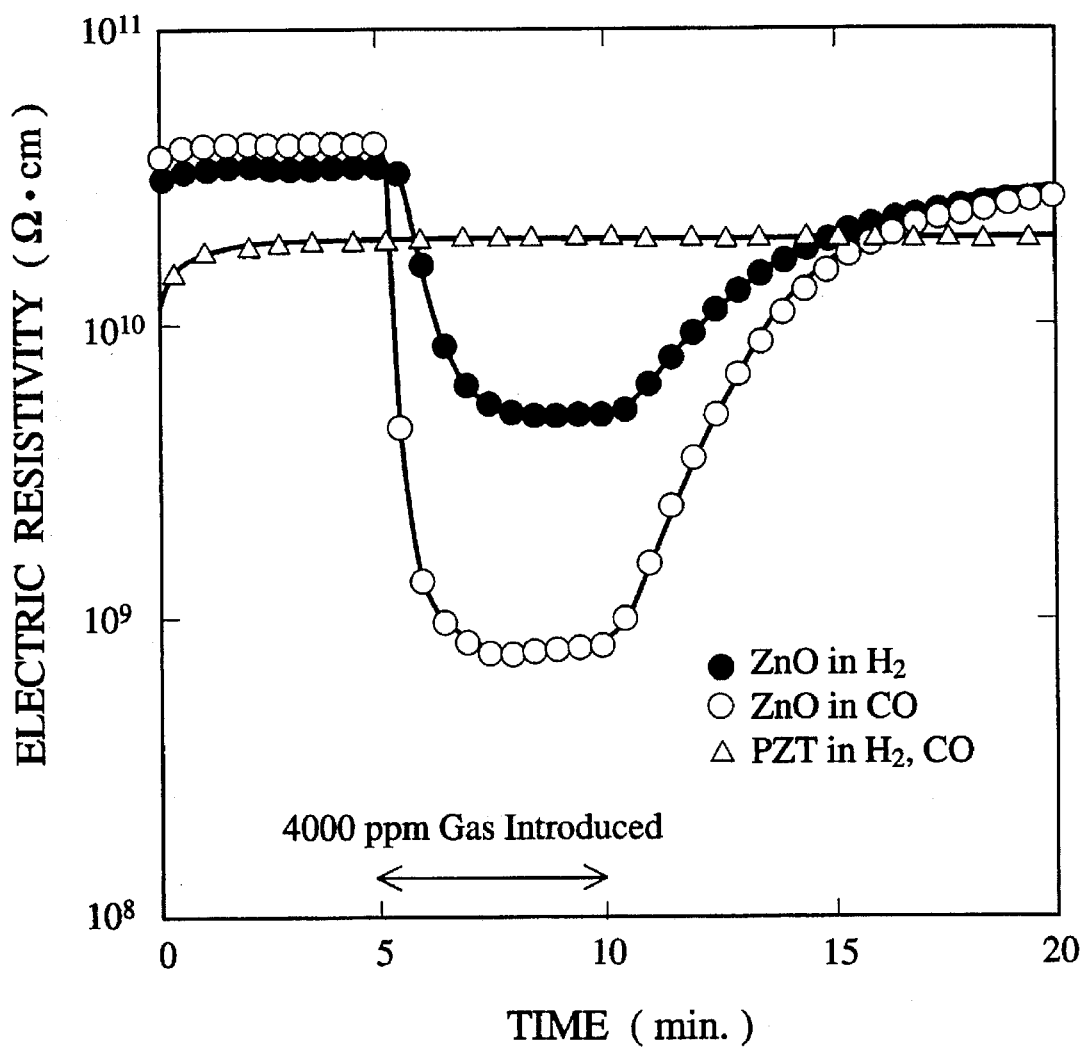
FIG. 4 is a graph showing the change of the electric resistance of ZnO ceramic sintered body and PZT sintered bodies with time in a case where the sintered body were placed in an air containing a CO gas or an air containing an $H_2$ gas.

As is clear from FIG. 4, the zinc oxide ceramic sintered body containing NiO and LiO (Sample E) showed a good sensitivity to both reducing gases, while the PZT sintered body (Sample F) was not sensitive to either of the reducing gases, showing an electric resistivity slightly exceeding about $10^{10}$ Ω·cm. Since the zinc oxide ceramic sintered body (Sample E) showed substantially the same level of an electric resistivity as that of the PZT sintered body (Sample F) when there was no reducing gas, it has been found that a good piezoelectric actuator which is not subjected to a bending displacement in a normal state (in the absence of a reducing gas) can be obtained by bonding the two sintered bodies. Further, it has been found that the addition of NiO and LiO provides a zinc oxide ceramic sintered body with a good sensitivity to a CO gas.

EXAMPLE 3

A 0.5-mm-thick PZT (Pb$_{0.995}$Nb$_{0.01}$(Zr$_{0.53}$Ti$_{0.47}$)$_{0.99}$O$_3$) sintered body prepared in the same manner as in Example 2 was coated with a glass frit having a softening point of 630° C. by a brush, stacked with a 0.5-mm thick zinc oxide ceramic green body (NiO: 10 mol %, LiO: 0.2 mol %) prepared in the same manner as in Example 2 and hot-pressed at 700° C. and 8 MPa for 1 hour. The resultant sintered body laminate was machined to obtain a piezoelectric actuator of 6 mm×11 mm×1 mm (thickness).

After coating the laminate with an Au electrode by sputtering on the zinc oxide ceramic sintered body side and with an Ag electrode by pasting on the PZT sintered body side, the laminate was baked. With lead wires connected to both electrodes, strain gauges were adhered to the sputtered Au electrode.

Figure 5:
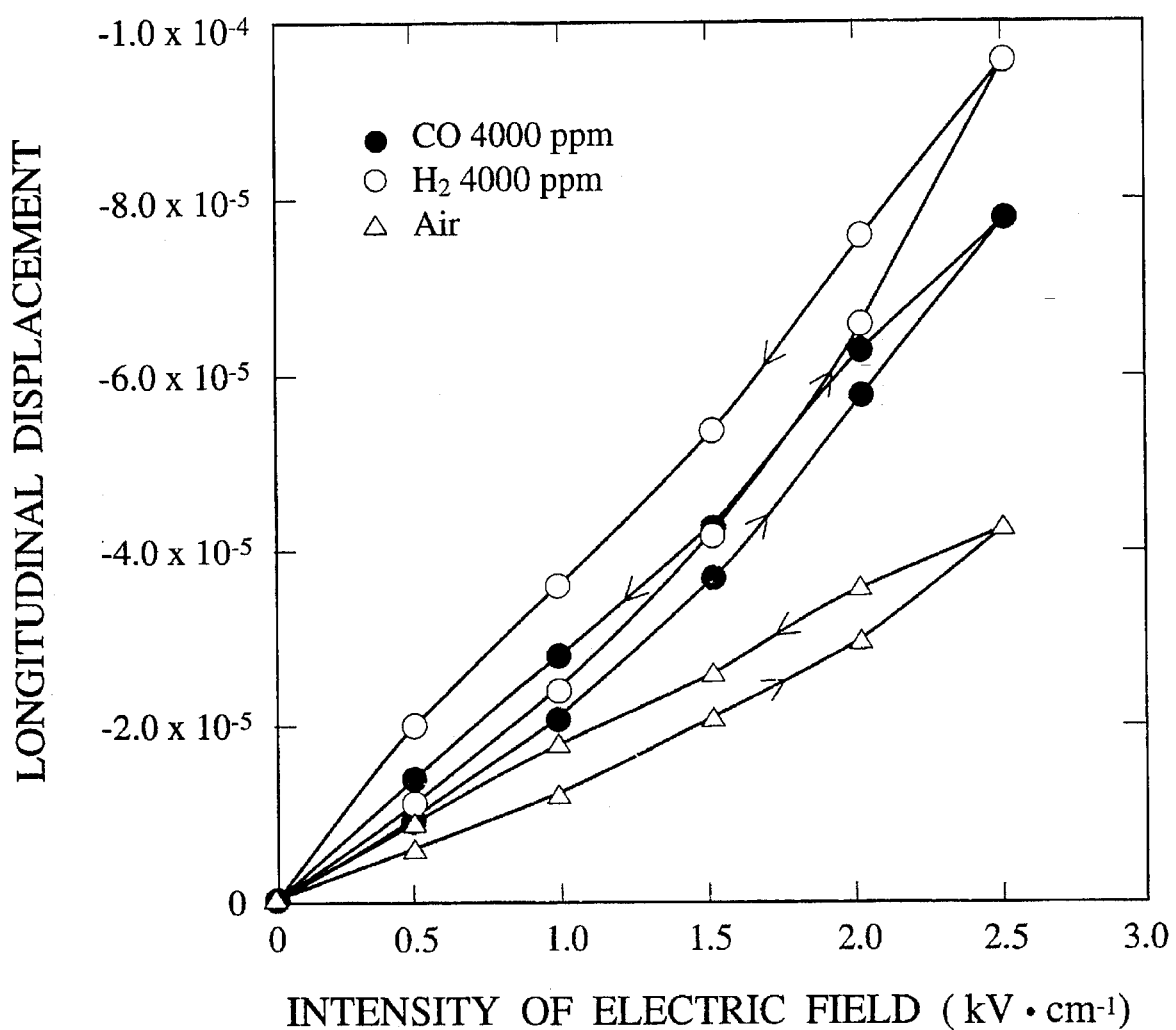
FIG. 5 is a graph showing the change of the longitudinal displacement of the piezoelectric actuator of Example 3 with an electric field applied in a case where the piezoelectric actuator was placed in an air, an air containing a CO gas or an air containing an $H_2$ gas.

The piezoelectric actuator thus obtained was placed in the same reactor as in Example 1, through which an air, an air containing 4000 ppm of a CO gas and an air containing 4000 ppm of an H$_2$ gas were caused to flow at 250° C. Under this condition, an electric field applied to both electrodes was changed from 0 kV/cm to 2.5 kV/cm to measure a longitudinal displacement of the piezoelectric actuator. The results are shown in FIG. 5. The longitudinal displacement is expressed by ΔL/L, wherein ΔL is a displaced distance in the longitudinal direction, and L is an initial longitudinal length of the piezoelectric actuator.

As is clear from FIG. 5, the piezoelectric actuator of the present invention showed a good sensitivity to both CO and H$_2$ gases. A ratio of the longitudinal displacement of the piezoelectric actuator in the presence of a CO gas or an H$_2$ gas to the longitudinal displacement of the piezoelectric actuator in the absence of a CO gas and an H$_2$ gas increased as the electric field applied increased. With this fact in mind, it has been found that the electric field is preferably 1–5 kV/cm from the practical point of view.

EXAMPLE 4

A 0.5-mm-thick PZT (Pb$_{0.995}$Nb$_{0.01}$(Zr$_{0.53}$Ti$_{0.47}$)$_{0.99}$O$_3$) sintered body prepared in the same manner as in Example 2 was coated with a glass frit having a softening point of 630° C. by a brush, stacked with a 0.5-mm-thick zinc oxide ceramic green body (NiO: 10 mol %, LiO: 0.2 mol %) prepared in the same manner as in Example 3 and hot-pressed at 700° C. and 8 MPa for 1 hour. The resultant sintered body laminate was machined to obtain a piezoelectric actuator of 3 mm×11 mm×1 mm (thickness).

After coating the laminate with an Au electrode by sputtering on the zinc oxide ceramic sintered body side and with an Ag electrode by pasting on the PZT sintered body side, the laminate was baked. With lead wires connected to both electrodes, strain gauges were adhered to the sputtered Au electrode.

The piezoelectric actuator thus obtained was placed in the same reactor as in Example 1, through which an air, an air containing 0.4 volume % of a CO gas, and an air containing 0.4 volume % of an $H_2$ gas were caused to flow at 250° C. Under this condition, an electric field applied to both electrodes was changed from 0 kV/cm to 250 kV/m to measure a bending displacement of the piezoelectric actuator with a non-contact laser sensor. The results are shown in FIG. 6.

Figure 6:
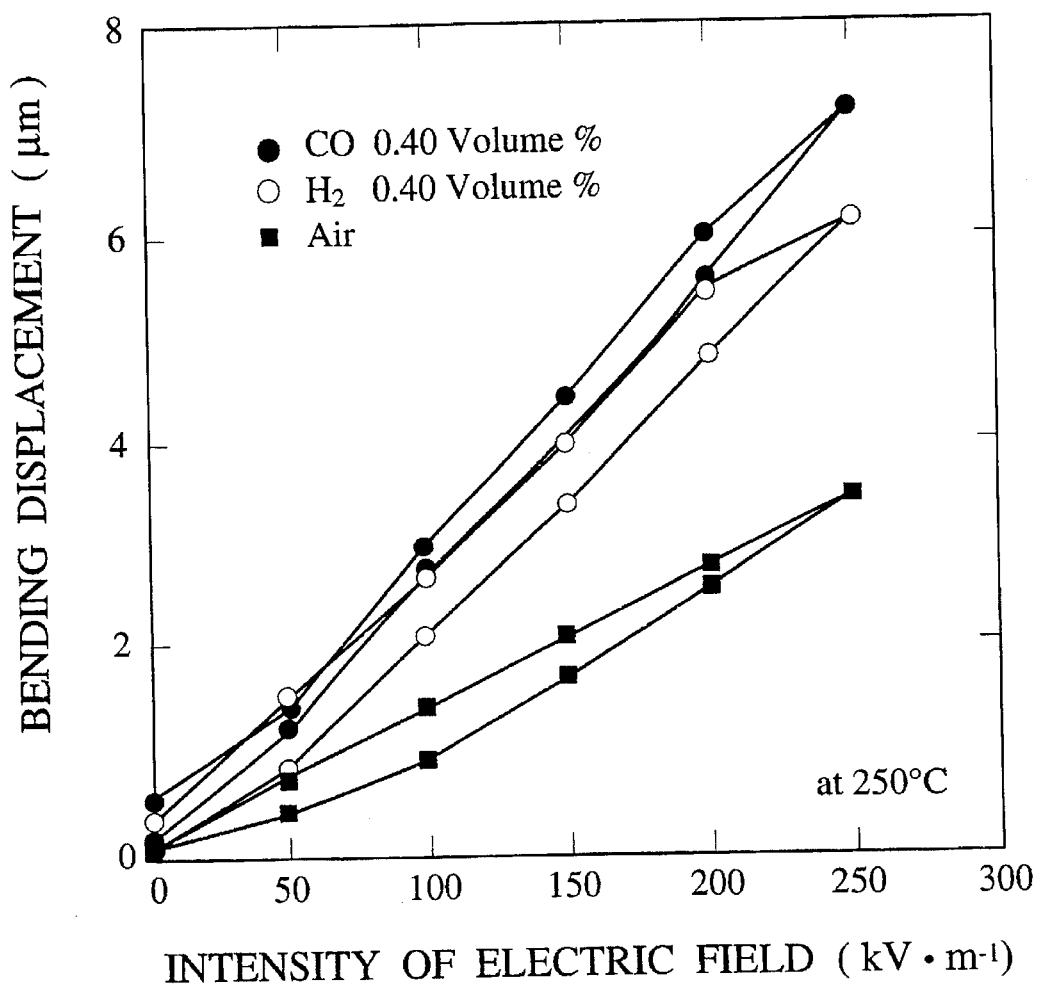
FIG. 6 is a graph showing the change of the bending displacement of the piezoelectric actuator of Example 4 with an electric field applied in a case where the piezoelectric actuator was placed in an air, an air containing a CO gas or an air containing an $H_2$ gas.

As is clear from FIG. 6, the piezoelectric actuator of the present invention showed a good sensitivity to both CO and $H_2$ gases. A ratio of the bending displacement of the piezoelectric actuator in the presence of a CO gas or an $H_2$ gas to the bending displacement of the piezoelectric actuator in the absence of a CO gas and an $H_2$ gas increased as the electric field applied increased.

As described above in detail, the piezoelectric actuator of the present invention shows a good sensitivity to reducing gases such as CO, $H_2$, etc. and is subjected to bending displacement in the presence of such a reducing gas. Accordingly, it can be utilized for valve-driving means for various valves, etc. which are operable in the presence of a reducing gas at a predetermined level or higher.

Further examples include movement of a damper in the form of a resilient plate to control the flow through a pipe as a function of CO concentration by use of the bending displacement provided by the piezoelectric actuator of the present invention. Another application is the control of a rotatable valve plate within a pipe (similar to a butterfly-type valve) for control of exhaust gas in an engine.

What is claimed is:

1. A piezoelectric actuator subjected to bending displacement by sensing a reducing gas, said piezoelectric actuator being composed of two regions bonded to each other, one of said regions being made of a material whose electric resistance varies by sensing a reducing gas, and the other of said regions being made of a piezoelectric material which is not sensitive to a reducing gas, an electrode being formed on an outer surface of each region to apply an electric field to said piezoelectric material.

2. The piezoelectric actuator according to claim 1, wherein said reducing gas-sensitive region is made of zinc oxide ceramics, and said piezoelectric material is lead titanate zirconate.

3. The piezoelectric actuator according to claim 2, wherein said zinc oxide ceramic contains 2–20 mol % of nickel oxide and 0.2–1 mol % of lithium oxide.

4. The piezoelectric actuator according to claim 1, wherein said reducing gas-sensitive region has a relative density of 40–80%, and said piezoelectric region has a relative density of 80–100%.

5. The piezoelectric actuator according to claim 2, wherein said reducing gas-sensitive region has a relative density of 40–80%, and said piezoelectric region has a relative density of 80–100%.

6. The piezoelectric actuator according to claim 3, wherein said reducing gas-sensitive region has a relative density of 40–80%, and said piezoelectric region has a relative density of 80–100%.

7. The piezoelectric actuator according to claim 6, wherein both of said reducing gas-sensitive region and said piezoelectric region are as thick as 100–1000 µm.

8. The piezoelectric actuator according to claim 6, wherein an electrode sputtered onto the surface of the reducing gas-sensitive region is 50–1000 Å, and an electrode on the surface of the piezoelectric region is 5–50 µm.

9. The piezoelectric actuator according to claim 1, wherein there is an intermediate layer between said reducing gas-sensitive region and said piezoelectric region, said intermediate layer being composed of a mixture of a material whose electric resistance varies by sensing a reducing gas and a piezoelectric material which is not sensitive to a reducing gas at a weight ratio of 8/2–2/8.

10. The piezoelectric actuator according to claim 3, wherein there is an intermediate layer composed of a mixture of ZnO/PZT at a weight ratio of 8/2–2/8 between said reducing gas-sensitive region and said piezoelectric region.

11. The piezoelectric actuator according to claim 4, wherein there is an intermediate layer composed of a mixture of ZnO/PZT at a weight ratio of 8/2–2/8 between said reducing gas-sensitive region and said piezoelectric region.

* * * * *